(12) United States Patent
Reynolds

(10) Patent No.: US 11,458,092 B2
(45) Date of Patent: *Oct. 4, 2022

(54) COMPOSITION WITH ENHANCED PASSENGER MOLECULE LOADING

(71) Applicant: NuVessl, Inc., Calgary (CA)

(72) Inventor: Jeffrey S. Reynolds, Seminole, FL (US)

(73) Assignee: NuVessl, Inc., Calgary (CA)

( * ) Notice: Subject to any disclaimer, the term of this patent is extended or adjusted under 35 U.S.C. 154(b) by 276 days.

This patent is subject to a terminal disclaimer.

(21) Appl. No.: 16/705,468

(22) Filed: Dec. 6, 2019

(65) Prior Publication Data

US 2020/0188323 A1 Jun. 18, 2020

Related U.S. Application Data

(60) Provisional application No. 62/890,940, filed on Aug. 23, 2019, provisional application No. 62/779,797, filed on Dec. 14, 2018.

(51) Int. Cl.

| *A61K 31/05* | (2006.01) |
|---|---|
| *A61K 31/352* | (2006.01) |
| *A61K 47/24* | (2006.01) |
| *A61K 47/44* | (2017.01) |
| *A61K 9/00* | (2006.01) |
| *A23L 33/105* | (2016.01) |
| *A23L 2/52* | (2006.01) |
| *A23P 10/35* | (2016.01) |
| *A61K 9/70* | (2006.01) |
| *A61K 9/127* | (2006.01) |
| *A61K 47/26* | (2006.01) |
| *A61K 36/185* | (2006.01) |

(52) U.S. Cl.
CPC .............. *A61K 9/0053* (2013.01); *A23L 2/52* (2013.01); *A23L 33/105* (2016.08); *A23P 10/35* (2016.08); *A61K 9/006* (2013.01); *A61K 9/0095* (2013.01); *A61K 9/1277* (2013.01); *A61K 9/7023* (2013.01); *A61K 31/05* (2013.01); *A61K 31/352* (2013.01); *A61K 47/24* (2013.01); *A61K 47/26* (2013.01); *A61K 47/44* (2013.01); *A23V 2002/00* (2013.01); *A61K 36/185* (2013.01)

(58) Field of Classification Search
CPC ...... A61K 31/05; A61K 31/352; A61K 47/24; A61K 47/44
See application file for complete search history.

(56) References Cited

U.S. PATENT DOCUMENTS

| 5,004,611 A | 4/1991 | Leigh |
|---|---|---|
| 5,009,819 A | 4/1991 | Popescu et al. |
| 5,269,979 A | 12/1993 | Fountain |
| 5,437,274 A | 8/1995 | Khoobehi et al. |
| 5,716,638 A | 2/1998 | Touitou |
| 5,814,343 A | 9/1998 | Jones et al. |
| 5,879,703 A | 3/1999 | Fountain |
| 5,885,921 A | 3/1999 | Krupey |
| 6,096,331 A | 8/2000 | Desai et al. |
| 6,203,778 B1 | 3/2001 | Brasch |
| 7,025,992 B2 | 4/2006 | Whittle |
| 8,377,989 B2 | 2/2013 | Ovokaitys et al. |
| 8,545,874 B2 | 10/2013 | Fountain |
| 8,545,875 B2 | 10/2013 | Fountain |
| 8,597,678 B2 | 12/2013 | Fountain |
| 8,778,401 B2 | 7/2014 | Shev et al. |

(Continued)

FOREIGN PATENT DOCUMENTS

| WO | WO9916426 | 4/1999 |
|---|---|---|
| WO | WO2017193169 | 11/2017 |

(Continued)

OTHER PUBLICATIONS

Godin, B., et al., "Ethosomes: New prospects in Transdermal Delivery," Critical Reviews in Therapeutic Drug Carrier Systems, vol. 20(1), (2003) pp. 63-102.

Gruner, S. et al., "Novel Multilayered Lipid Vesicles: Comparison of Physical Characteristics of Multilamellar Liposomes and Stable Pluilamellar Vesicles," Biochemistry, vol. 24 (1985) pp. 2833-2842.

Guzman, C., et al., "Antibody Responses in the Serum and Respiratory Tract of Mice Following Oral Vaccination with Liposomes Coated with Filamentous Hemagglutinin and Pertussis Toxoid," Infection and Immunity, vol. 61, No. 2, (1993) pp. 573-579.

(Continued)

*Primary Examiner* — Matthew P Coughlin
(74) *Attorney, Agent, or Firm* — Hemingway & Hansen, LLP; D. Scott Hemingway; Elizabeth P. Hartman

(57) ABSTRACT

A composition comprising surfactant-enhanced phospholipid vesicles with one or more cannabinoid substance encapsulated therein is disclosed, wherein one or more surfactant is utilized for enhancing loading and increasing encapsulation efficiency of cannabinoid passenger molecules within phospholipid structures. A method is disclosed for making a surfactant-enhanced phospholipid vesicles with one or more cannabinoid substance encapsulated therein, wherein one or more surfactant is used for enhancing loading and increasing encapsulation efficiency of passenger molecules in phospholipid structures. A method of using surfactant-enhanced phospholipid vesicles with one or more cannabinoid substance encapsulated therein is disclosed wherein one or more surfactant enhances loading and increases encapsulation efficiency of cannabinoid substances in phospholipid structures. A composition and method of making surfactant-enhanced phospholipid vesicles with one or more lipophilic passenger substance encapsulated therein is disclosed wherein one or more surfactant is utilized for enhancing loading and increasing encapsulation efficiency of passenger molecules within phospholipid structures.

26 Claims, No Drawings

(56) References Cited

U.S. PATENT DOCUMENTS

| | | | |
|---|---|---|---|
| 8,808,734 | B2 | 8/2014 | Winnicki |
| 9,095,555 | B2 | 8/2015 | Winnicki |
| 9,265,724 | B2 * | 2/2016 | Murty ............... A61K 9/4858 |
| 9,364,434 | B2 | 6/2016 | Fountain |
| 9,399,015 | B2 | 9/2016 | Fountain |
| 9,480,650 | B2 | 11/2016 | Fountain |
| 9,603,801 | B2 | 3/2017 | Barnett et al. |
| 9,635,876 | B2 | 5/2017 | Fountain |
| 9,987,234 | B2 | 6/2018 | Fountain |
| 9,993,439 | B2 | 6/2018 | Gu et al. |
| 10,028,919 | B2 | 7/2018 | Kaufman |
| 10,052,303 | B2 | 8/2018 | Winnicki |
| 10,058,515 | B2 | 8/2018 | Yeshurun |
| 10,080,736 | B2 | 9/2018 | Kleidon et al. |
| 10,240,115 | B2 | 3/2019 | Fountain |
| 10,246,672 | B2 | 4/2019 | Fountain |
| 10,266,800 | B2 | 4/2019 | Fountain |
| 2001/0006643 | A1 | 7/2001 | Hope |
| 2005/0191330 | A1 | 9/2005 | Huglin |
| 2009/0004285 | A1 | 1/2009 | Yu et al. |
| 2009/0311295 | A1 | 12/2009 | Mathiowitz et al. |
| 2014/0302148 | A1 * | 10/2014 | Winnicki ............ A61K 47/36 424/489 |
| 2018/0169061 | A1 | 6/2018 | Gumudavelli et al. |
| 2018/0296493 | A1 | 10/2018 | Kaufman |
| 2018/0325861 | A1 | 11/2018 | Domb et al. |
| 2018/0344644 | A1 | 12/2018 | Podaralla et al. |
| 2018/0353463 | A1 | 12/2018 | Winnicki |
| 2018/0360736 | A1 | 12/2018 | Obied et al. |
| 2019/0021997 | A1 | 1/2019 | Tung |

FOREIGN PATENT DOCUMENTS

| | | |
|---|---|---|
| WO | WO2018061007 | 4/2018 |
| WO | WO2018152334 | 8/2018 |

OTHER PUBLICATIONS

International Preliminary Report on Patentability for corresponding Application PCT/ US2006/048770; dated Jan. 29, 2008.
Komatsu, H. et al., "Effects of ethanol on permeability of phosphatidylcholine/cholesterol mixed with liposomal membranes," Chemistry and Physics of Lipids, vol. 85 (1997) pp. 67-74.
Masson, G., "Characterization of Small Lipid Vesicles Prepared by Microfluidization," Progress in Colloid & Polymer Science, vol. 79, (1989) pp. 49-51.
Maurer, N. et al., "Spontaneous entrapment of polynucleotides upon electrostatic interaction with ethanol-destabilized cationic liposomes," Biophysical Journal, vol. 80 (2001) pp. 2310-2326.
Nounou, M. et al., "In vitro release of hydrophilic and hydrophobic drugs from liposomal dispersions and gels." Acta Pharma 56 (2006) pp. 311-324.
Panico, A. et al., "Preparation of liposome formulations containing immunomodulatory peptides." Pharmaceutica Acta Helvetiae 72 (1997) pp. 1-10.
Philippot, J. R., et al., "Liposomes as Tools in Basic Research and Industry." CRC Press, (1995) pp. 7-8.
Schnyder, A., et al., "Drug Transport to Brain with Targeted Liposomes." NeuroRx, vol. 2, No. 1 (2005) pp. 99-107.
Singh, A.K., et al., "Applications of Antibody and Fluorophore-derivatized Liposomes to Heterogeneous Immunoassays for D-dimer." Biotechnology Progress, vol. 12, No. 2 (1996) pp. 272-280.
Zheng, J.Y., et al., "Pulmonary Peptide Delivery: Effect of Taste-Masking Excipients on Leuprolide Suspension Metered-Dose Inhalers," Pharmaceutical Development and Technology, vol. 6(4) (2001) pp. 521-530.
Ghaghada, Ketan, et al., "T1 Relaxivity of Core-encapsulated Gadolinium Liposomal Contrast Agents—Effects of Liposome Size and Internal Gadolinium Concentration," Acad. Radiol. (2008) 15(10), 1259-1263.
Kremer, et al., "Vesicles of Variable Diameter Prepared by Modified Injection Method," Biochemistry 16(1977) pp. 3932-3935.
Pillman et al., "Effects of Ethanol on the Organization of Phosphocholine Lipid Bilayers," J. Phy. Chem B (2010) 114, pp. 3840-3846.
Yang et al., "On the Stability of Liposomal Cantansomes in Aqueous Alcohol Solution," Langmuir (2008) pp. 1695-1700.
Zhao et al., "Size-induced Enhancement of Chemical Exchange Saturation Transfer (CEST) Contrast in Liposomes," J A. Chem Soc (2008) 130, pp. 5178-5184.
Berger, et al., "Filter extrusion of liposomes using different devices: comparisons of liposome size, encapsulation efficiency, and process characteristics," Int J Pharm, vol. 223, n.1-2 (2001), pp. 55-68.
Dos Santos, et al. "pH gradient loading of anthracyclines into cholesterol-free liposomes: enhancing drug loading rates through use of ethanol," Biochemica et Biophysica Acta 1661 (2004), pp. 47-60.
Muller, et al., "Solid lipid nanoparticles (SLN) for controlled drug delivery—a review of the state of the art," EP J of Pharma & Biopharma 50 (2000), pp. 161-177.
Karschner, Erin, et al., "Plasma Cannabinoid Pharmacokinetics following Controlled Oral delta9-Tetrahydrocannabinol and Oromucosal Cannabis Extract Administration," Clinical Chemistry, ClinicalTrials. gov, clinicaltrials.gov/ct2/show/NCT01893424. (Dec. 2010).
Karschner, Erin, et al., "Plasma Cannabinoid Pharmacokinetics following Controlled Oral delta9-Tetrahydrocannabinol and Oromucosal Cannabis Extract Administration," Clinical Chemistry 57:1, 66-75 (2011).
Schatman, Michael E., "Medical Marijuana: The State of the Science." Medscape, (Feb. 6, 2015).
Huestis, Marilyn A. "Human Cannabinoid Pharmacokinetics." Chemistry & Biodiversity, vol. 4, 1770-1804, (2007), Wiley Online Library, onlinelibrary.wiley.com/doi/10.1002/cbdv.200790152/references.
Zhornitsky, Simon, et al. "Cannabidiol in Humans—The Quest for Therapeutic Targets." Pharmaceuticals 2012, 5, 529-552; doi:1:10. 3390/ph5050529, MDPI, Molecular Diversity Preservation International, (May 21, 2012 ).
Sachs, Jane, et al. "Safety and Toxicology of Cannabinoids." Neurotherapeutics, Springer New York, (Jul. 1, 2016), utah.pure. elsevier.com/en/publications/sarety-and-toxicology-of-cannabinoids.
Iffland, Kerstin et al.—"An Update on Safety and Side Effects of Cannabidiol—A Review of Clinical Data and Relevant Animal Studies," Cannabis and Cannabinoid Research, vol. 2.1, 2017, (Jun. 1, 2017), www.scribd.com/document/354665879/Update-on.Safety-and-Side-Effects-of-Cannabidiol.
Mayo Clinic, "Marijuana," Mayo Foundation for Medical Education and Research (Oct. 24, 2017), https://www.mayoclinic.org/drugs-supplements-marijuana/art-20364974.

* cited by examiner

COMPOSITION WITH ENHANCED PASSENGER MOLECULE LOADING

CROSS REFERENCE TO RELATED APPLICATIONS

This application claims the benefit of U.S. Provisional Application Nos. 62/779,797 filed Dec. 14, 2018, and 62/890,940, filed Aug. 23, 2019, which are incorporated by reference into this utility patent application.

STATEMENT REGARDING FEDERALLY SPONSORED RESEARCH OR DEVELOPMENT

Not applicable.

TECHNICAL FIELD OF INVENTION

This invention relates to the field of using surfactants to enhance encapsulation of lipophilic passenger molecules in nano-sized phospholipid structures.

BACKGROUND OF THE INVENTION

Active components have been sequestered in phospholipid particles using prior art methods and compositions, but these known prior art methods and compositions fail to retain all types of active components, especially at higher concentrations, in a solubilized state for extended periods of time, which decreases the overall stability and usability of the preparations.

For instance, known nanolipid particle prior art, U.S. Pat. Nos. 8,597,678; 8,545,574; 8,545,575; 9,480,650; 9,364,434; 9,399,015; and 9,897,234, to Fountain, fail to solve the present problem of precipitation for certain types of lipophilic passenger molecules. Moreover, these Fountain prior art references rely on aqueous-diluted formulations using an aqueous phase to close the particles with the passenger molecules encapsulated within the particles, which is believed to contribute to the precipitation problem for certain lipophilic passengers. So, it has been found that for certain lipophilic passenger molecules, such aqueous-diluted nano-lipid formulations are only stable for up to three days using the prior art methods and compositions. Certain lipophilic passengers crystallize out of solution and settle to the bottom of the formulation rendering the formulation usable for only the first day or two after preparation. This precipitation necessitates preparation of materials at the point of use and in small batch quantities over the course of multiple days, presenting logistical difficulties in the preparation and use of uniform materials for study or administration. And, formulations prepared at point of use are totally inadequate for large-scale use, which prevents a wider use of these lipophilic passengers in lipid particles.

What is needed is a method and composition that solves the precipitation problem and improves the physical stability of the lipophilic passenger formulations over extended shelf-life periods of time, thereby allowing for advance preparation of a stable formulation of lipophilic passengers.

SUMMARY OF THE INVENTION

In the following manner, the problems encountered by the prior art systems, including Fountain, have been solved. Disclosed herein is a novel method of encapsulating lipophilic passenger molecules in surfactant-enhanced phospholipid vesicles utilizing one or more surfactants as an encapsulating agent, rather than water, to prepare a passenger encapsulate having surfactant-enhanced phospholipid vesicles with lipophilic passengers encapsulated therein. Disclosed herein are compositions of surfactant-enhanced phospholipid vesicles with encapsulated lipophilic passengers, methods of making surfactant-enhanced phospholipid vesicles with encapsulated lipophilic passengers, and methods of using surfactant-enhanced phospholipid vesicles with encapsulated lipophilic passengers. The claimed surfactant-enhanced phospholipid vesicles have up to 25% (w/w) surfactant and less than 2% (w/w) water. In the surfactant-enhanced phospholipid vesicles prepared according to the present invention, the passenger molecules remain encapsulated in the vesicles even when passenger encapsulate is combined or diluted with excipient ingredients or water in a preparation for administration to a subject.

Compositions are disclosed with enhanced loading of passenger molecules in phospholipid based vesicles utilizing a surfactant to increase the encapsulation concentration of passenger molecules while decreasing precipitation of the encapsulated passenger. The surfactant enhancers are especially efficacious for increasing encapsulation of lipophilic passenger molecules in the phospholipid vesicles. Passenger molecules that may benefit from enhanced encapsulation include, but are not limited to, cannabinoids, cannabidiol (CBD), tetrahydrocannabinol (THC), menthol, lidocaine, aspirin, ibuprofen, acetaminophen, antifungals, and retinoids. Of particular interest as passengers are cannabinoids, such as cannabidiol (CBD) and tetrahydrocannabinol (THC). Cannabinoids can be naturally derived from botanical sources, such as *Cannabis sativa* or *Cannabis indica*, including marijuana and/or hemp varieties, or can be synthetically-derived.

Cannabinoids are a class of typically lipophilic substances that, as passenger molecules, benefit from enhanced loading in phospholipid based structures with the use of surfactants. Utilizing surfactant enhancement allows for a substantial increase in the concentration of cannabinoid compounds that can be encapsulated as passengers in the phospholipid vesicles. When surfactants are used to enhance encapsulation of cannabinoid passengers, the preparation remains stably encapsulated and precipitation of the cannabinoids does not occur even at very high concentrations. The enhancements are achieved for both lipophilic cannabinoid substances and hydrophilic cannabinoid substances, such as crystalline CBD. Cannabinoid encapsulates having surfactant-enhanced phospholipid vesicles with one or more cannabinoid encapsulated therein can be advantageously used to administer cannabinoids to a subject by oral, transmucosal, or transdermal routes. Once the cannabinoid passenger is fully encapsulated, the cannabinoid encapsulate can be diluted to the desired dosage without precipitation of the cannabinoid from the preparation.

Disclosed herein is a method of making surfactant-enhanced phospholipid vesicles encapsulating one or more cannabinoid. The method comprises the steps of providing one or more cannabinoid substance; providing a phospholipid stock solution having phospholipids, ethanol and water, where water comprises 5% or less by weight of the phospholipid stock solution; diluting the phospholipid stock solution with a quantity of ethanol to produce an ethanol-diluted phospholipid stock, combining the cannabinoid with the ethanol-diluted phospholipid stock to produce a cannabinoid-phospholipid stock; and mixing the cannabinoid-phospholipid stock with a surfactant. A cannabinoid encapsulate results having one or more surfactant-enhanced phospholipid vesicle encapsulating one or more cannabinoid substance therein, with the cannabinoid encapsulate having less than 2% water (w/w).

Surfactants useful in the method are Polysorbates, Polysorbate (Tween) 20, Polysorbate (Tween) 80, PEG esters of hydrogenated castor oil, PEG-40 hydrogenated castor oil, Polyethylene Glycols, Ethoxylated ether alcohols, Propylene Glycols, PPG esters, Sodium, Potassium or Ammonium Salts of Fatty Acids, and derivatives or combinations thereof. Optionally, the surfactant is Polysorbates and derivatives, PEG esters of hydrogenated castor oil and derivatives, and combinations thereof. Optionally, the surfactant is Polysorbate (Tween) 20, Polysorbate (Tween) 80, PEG-40 hydrogenated castor oil, and combinations thereof. The surfactant comprises up to 25% of the cannabinoid encapsulate. Optionally, the surfactant is 0.5% to 20% of the cannabinoid encapsulate.

Passenger molecules useful for the invention are synthetically-derived cannabinoids or cannabinoid and non-cannabinoid substances derived from *Cannabis* spp., primarily *Cannabis sativa* and *Cannabis indica*. Among the known *Cannabis*-derived substances that may be used for the invention are Cannabidiol (CBD), Tetrahydrocannabinol (THC), Cannabigerol (CBG), Cannabidiolic Acid (CBDA), Tetrahydrocannabinolic Acid (THCA), Cannabinol (CBN), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol monomethyl ether (CBGM), Cannabielsoin (CBE), Cannabicitran (CBT), *Cannabis*-derived terpenes, *Cannabis*-derived flavonoids, whole plant extracts of *Cannabis sativa* or *Cannabis indica*, and combinations thereof. Optionally, the *Cannabis*-derived substances are cannabidiol (CBD), tetrahydrocannabinol (THC), whole plant extract of *Cannabis sativa*, whole plant extract of *Cannabis indica*, and combinations thereof. The cannabinoid encapsulate has a cannabinoid concentration of 3 mg/mL to 300 mg/mL.

A phospholipid stock solution useful for the method has phospholipids, ethanol and water, wherein water is 5% (w/w) or less of the stock. Optionally, the phospholipid stock solution has 10-20% (w/w) phospholipids, 75-89% (w/w) ethanol, and 1-5% water (w/w). The phospholipid stock solution is diluted with a quantity of ethanol up to 75% (w/w) prior to addition of or in combination with the cannabinoid passenger substance.

Also disclosed is a composition of surfactant-enhanced phospholipid vesicles with one or more cannabinoid substance encapsulated therein prepared according to the described method. The composition comprises one or more synthetic or botanical-derived cannabinoid substance encapsulated in surfactant-enhanced phospholipid vesicles, the cannabinoid substance concentration being from 3.0 mg/mL to 300 mg/mL, and the surfactant-enhanced phospholipid vesicles having one or more surfactant, phospholipids, ethanol, and water, wherein the one or more surfactant is up to 25% (w/w) of the composition, and the water is less than 2% (w/w) of the composition. The surfactant is optionally, Polysorbates and derivatives, PEG esters of hydrogenated castor oil and derivatives, or combinations thereof. Optionally, the surfactant is Polysorbate (Tween) 20, Polysorbate (Tween) 80, PEG-40 hydrogenated castor oil, or combinations thereof. Optionally, the one or more cannabinoid substance is botanical-derived cannabidiol (CBD), tetrahydrocannabinol (THC), *Cannabis*-derived terpenes, *Cannabis*-derived flavonoids, a whole plant extract of *Cannabis sativa*, a whole plant extract of *Cannabis indica*, and combinations thereof. Optionally, the one or more cannabinoid substance is synthetically-derived cannabidiol (CBD), tetrahydrocannabinol (THC), and combinations thereof.

Also disclosed are methods of using the composition of surfactant-enhanced phospholipid vesicles with one or more cannabinoid substance encapsulated therein. Methods of using the composition include the steps of providing a cannabinoid encapsulate having one or more synthetic or botanical-derived cannabinoid substance encapsulated in one or more surfactant-enhanced phospholipid vesicles having phospholipids, ethanol, water, and one or more surfactant selected from Polysorbates and derivatives, PEG esters of hydrogenated castor oil and derivatives, and combinations thereof, wherein the cannabinoid substance in the cannabinoid encapsulate has a concentration of 3 mg/mL to 300 mg/mL, and the cannabinoid encapsulate has less than 2% water (w/w) and up to 25% (w/w) of the surfactant; and administering a quantity of an oral preparation having 1 mg to 100 mg of cannabinoid substance to a subject. Optionally, the composition is delivered orally as a drinkable beverage of about 1.5-12 ounces, drinkable shot of about less than 1.5 ounce, or swish and swallow preparation of about less than 1.0 ounce. Optionally, the composition is administered transmucosally to the oral cavity of a subject as a liquid drop, liquid spray, aerosol, liquid shot, gel, paste, lozenge, gum, gummy candy, hard candy, orally dissolving strip, tablet, or swish and swallow preparation. Optionally, the composition is administered topically or transdermally to the epidermis of a subject as a cream, lotion, ointment, wax, topically applied spray, gel, balm, or transdermal patch.

The preparations for oral, transmucosal, topical, and transdermal delivery may further comprise one or more excipient ingredients suitable for a preparation delivered orally, transmucosally, topically, or transdermally wherein the excipient ingredients are for stabilization, appearance, flavoring, or dilution of the preparation. The oral, transmucosal topical, or transdermal preparations may further comprise one or more sweeteners, flavorings, vitamins, minerals, herbal ingredients and extracts, fruit extracts, vegetable extracts, spices or spice extracts, caffeine, amino acids, or nutraceutical ingredients.

DETAILED DESCRIPTION

Disclosed herein are Surfactant-Enhanced Phospholipid Vesicles (SEPV), which are nano-sized phospholipid vesicles that employ a surfactant to complete the encapsulation process for lipophilic passenger substances, which enhances the encapsulation efficiency and prevents precipitation of the passenger molecules.

Disclosed herein is a method of making surfactant-enhanced phospholipid vesicles encapsulating one or more cannabinoid or *Cannabis* spp.-derived substance. The method comprises the steps of providing one or more cannabinoid or *Cannabis* spp.-derived substance; providing a phospholipid stock solution having phospholipids, ethanol and water, where water comprises 5% or less by weight of the phospholipid stock solution; diluting the phospholipid stock solution with a quantity of ethanol to produce an ethanol-diluted phospholipid stock, combining the cannabinoid or *Cannabis* spp.-derived substance with the ethanol-diluted phospholipid stock to produce a cannabinoid-phospholipid stock; and mixing the cannabinoid-phospholipid stock with a surfactant. A cannabinoid encapsulate results having one or more surfactant-enhanced phospholipid vesicle encapsulating one or more cannabinoid or *Cannabis* spp.-derived substance therein, with the cannabinoid encapsulate having less than 2% water (w/w).

Also disclosed is a composition of surfactant-enhanced phospholipid vesicles with one or more cannabinoid or *Cannabis* spp.-derived substance encapsulated therein prepared according to the described method. The composition comprises one or more cannabinoid or *Cannabis* spp.-derived substance encapsulated in surfactant-enhanced phospholipid vesicles, the cannabinoid or *Cannabis* spp.-derived substance concentration being from 3.0 mg/mL to 300 mg/mL, and the surfactant-enhanced phospholipid vesicles having one or more surfactant, phospholipids, ethanol, and water, wherein the one or more surfactant is up to 25% (w/w) of the composition, and the water is less than 2% (w/w) of the composition. The surfactant is optionally, Polysorbates and derivatives, PEG esters of hydrogenated castor oil and derivatives, or combinations thereof. Optionally, the surfactant is Polysorbate (Tween) 20, Polysorbate (Tween) 80, PEG-40 hydrogenated castor oil, or combinations thereof. Optionally, the one or more cannabinoid or *Cannabis* spp.-derived substance is *Cannabis sativa*-derived cannabidiol (CBD), *Cannabis sativa*-derived tetrahydrocannabinol (THC), *Cannabis sativa*-derived terpenes, *Cannabis sativa*-derived flavonoids, a whole plant extract of *Cannabis sativa*-derived substance, and combinations thereof. Optionally, the one or more cannabinoid or *Cannabis* spp.-derived substance is *Cannabis indica*-derived cannabidiol (CBD), *Cannabis indica*-derived tetrahydrocannabinol (THC), *Cannabis indica*-derived terpenes, *Cannabis indica*-derived flavonoids, a whole plant extract of *Cannabis indica*-derived substance, and combinations thereof. Optionally, the one or more cannabinoid substance is a synthetically-derived cannabinoid, synthetically-derived cannabidiol (CBD), synthetically-derived tetrahydrocannabinol (THC), and combinations thereof Also disclosed are methods of using the composition of surfactant-enhanced phospholipid vesicles with one or more cannabinoid or *Cannabis* spp.-derived substance encapsulated therein. The method of using the composition includes the steps of providing a cannabinoid encapsulate having one or more cannabinoid or *Cannabis* spp.-derived substance encapsulated in one or more surfactant-enhanced phospholipid vesicles having phospholipids, ethanol, water, and one or more surfactant selected from Polysorbates and derivatives, PEG esters of hydrogenated castor oil and derivatives, and combinations thereof, wherein the cannabinoid or *Cannabis* spp.-derived substance in the cannabinoid encapsulate has a concentration of 3 mg/mL to 300 mg/mL, and the cannabinoid encapsulate has less than 2% water (w/w) and up to 25% (w/w) of the surfactant; and administering a quantity of the oral preparation having 1 mg to 100 mg of cannabinoid or *Cannabis* spp.-derived substance to a subject. Optionally, the composition is delivered orally or transmucosally to a subject. Optionally, the composition is delivered orally as a drinkable beverage of about 1.5-12 ounces, drinkable shot of about less than 1.5 ounce, or swish and swallow preparation of about less than 1.0 ounce. Optionally, the composition is administered transmucosally to the oral cavity of a subject as a liquid drop, liquid spray, aerosol, liquid shot, gel, paste, lozenge, gum, gummy candy, hard candy, orally dissolving strip, tablet, or swish and swallow preparation. Optionally, the composition is administered topically or transdermally to the epidermis of a subject. Optionally, the composition is administered topically or transdermally to the epidermis of a subject as a cream, lotion, ointment, wax, topically applied spray, gel, balm or transdermal patch.

Surfactants useful in the method are Polysorbates, Polysorbate (Tween) 20, Polysorbate (Tween) 80, PEG esters of hydrogenated castor oil, PEG-40 hydrogenated castor oil, Polyethylene Glycols, Ethoxylated ether alcohols, Propylene Glycols, PPG esters, Sodium, Potassium or Ammonium Salts of Fatty Acids, and derivatives or combinations thereof. Optionally, the surfactant is Polysorbates and derivatives, PEG esters of hydrogenated castor oil and derivatives, and combinations thereof. Optionally, the surfactant is Polysorbate (Tween) 20, Polysorbate (Tween) 80, PEG-40 hydrogenated castor oil, and combinations thereof. The surfactant comprises up to 25% of the cannabinoid encapsulate. Optionally, the surfactant is 0.5% to 20% of the cannabinoid encapsulate.

Passenger molecules useful for the invention are synthetically-derived cannabinoids or cannabinoid and non-cannabinoid substances derived from *Cannabis* spp., primarily *Cannabis sativa* and *Cannabis indica*. Among the known *Cannabis*-derived substances that may be used for the invention are Cannabidiol (CBD), Tetrahydrocannabinol (THC), Cannabigerol (CBG), Cannabidiolic Acid (CBDA), Tetrahydrocannabinolic Acid (THCA), Cannabinol (CBN), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol monomethyl ether (CBGM), Cannabielsoin (CBE), Cannabicitran (CBT), *Cannabis*-derived terpenes, *Cannabis*-derived flavonoids, whole plant extracts of *Cannabis sativa* or *Cannabis indica*, and combinations thereof. Optionally, the *Cannabis*-derived substances are cannabidiol (CBD), tetrahydrocannabinol (THC), whole plant extract of *Cannabis sativa*, whole plant extract of *Cannabis indica*, and combinations thereof. The cannabinoid encapsulate has a cannabinoid concentration of 3 mg/mL to 300 mg/mL.

The phospholipid stock solution useful for the method has phospholipids, ethanol and water, wherein water is 5% (w/w) or less of the stock. Optionally, the phospholipid stock solution has 10-20% (w/w) phospholipids, 75-89% (w/w) ethanol, and 1-5% (w/w) water. The phospholipid stock solution is diluted with a quantity of ethanol up to 75% (w/w) prior to addition of or in combination with the cannabinoid passenger substance.

Compositions with enhanced loading of cannabinoid passenger are disclosed wherein the compositions may be used as oral preparations, either alone or in conjunction with a beverage product, for oral delivery of synthetically or botanically-derived cannabinoids or other compounds derived from *Cannabis* spp. Compositions with enhanced loading of cannabinoid passenger are also disclosed wherein the compositions may be used as topical or transdermal preparations applied to epidermis for delivery of synthetically or botanically-derived cannabinoids or other compounds derived from *Cannabis* spp.

Phospholipid vesicles are generally sphere-shaped vesicles with one or more phospholipid layer surrounding a core space which may contain passenger molecules sequestered therein. The vesicles can be used as delivery vehicles for passenger molecules. Passenger molecules are active substances that can be sequestered or encapsulated in the phospholipid vesicles for delivery of a substance to a subject. The load-enhancing surfactant used with phospholipid vesicles as described herein is particularly beneficial for encapsulation of passengers that are lipophilic. Surfactants (i.e. surface-active agents) are compounds that are partly hydrophilic (water-soluble) and partly lipophilic (soluble in lipids or oils) and lower the surface tension (or interfacial tension) between two liquids, between a gas and a liquid, or between a liquid and a solid. Surfactants are usually organic compounds that are amphiphilic, consisting of a hydrophilic head group and a hydrophobic tail, and they generally are suitable compounds for use in complex mixtures. The surfactants useful for the present invention exhibit a very low toxicity level and are acceptable for use in pharmaceuticals, cosmetics and food products.

Particular surfactants in precisely controlled amounts have been found that will enhance stability of passenger molecules in the phospholipid vesicles. These surfactants not only prevent precipitation of the passenger, but also allow for increased passenger molecule loading into the surfactant-enhanced phospholipid vesicles up to more than a hundred-fold over the previous water-based models.

Preparation of nanolipid particles typically requires the use of an aqueous phase to complete the encapsulation and close the vesicles with the passengers sequestered therein. In the present invention, a surfactant is utilized to close the vesicles and complete the encapsulation phase. An aqueous phase is not required for preparation of the composition, however, after passengers are fully encapsulated in the composition, the final composition of surfactant-enhanced phospholipid vesicles can be advantageously combined with an aqueous-based delivery system without precipitation or loss of the encapsulated passengers from the vesicles or degradation or the vesicles.

Compositions are disclosed with enhanced loading of passenger molecules in surfactant-enhanced phospholipid based vesicles utilizing a surfactant to increase the encapsulation concentration of passenger molecules while decreasing precipitation of the encapsulated passenger. The surfactant enhancers are especially efficacious for increasing encapsulation of lipophilic passenger molecules in the phospholipid vesicles. Passenger molecules that may benefit from enhanced encapsulation include, but are not limited to, cannabinoids, cannabidiol (CBD), tetrahydrocannabinol (THC), menthol, lidocaine, aspirin, ibuprofen, acetaminophen, antifungals, and retinoids.

Of particular interest as passengers are cannabinoids substances derived from plants or synthetically-derived. Plant-derived cannabinoids may be derived from *Cannabis* species, including *Cannabis sativa* and *Cannabis indica*. Cannabinoids are a class of typically lipophilic substances that as passenger molecules benefit from enhanced loading in phospholipid based structures with the use of surfactants. Utilizing surfactant enhancement allows for a substantial increase in the concentration of cannabinoid compounds that can be encapsulated as passengers in the phospholipid vesicles. When surfactants are used to enhance encapsulation of cannabinoid passengers, the preparation remains stably encapsulated and precipitation of the cannabinoids does not occur, even at very high concentrations. The enhancements are achieved for both lipophilic cannabinoid substances and hydrophilic cannabinoid substances, such as crystalline CBD, but are especially advantageous for lipophilic passenger substances.

A liquid dosage form enabling delivery of cannabidiol (CBD) using nanolipid particle technology to encapsulate the CBD for oral administration was utilized as part of a pharmacokinetic (PK) bioavailability study. In this aqueous-diluted formulation, crystals were observed in stored samples within a few days of preparation of the solution. It was found that the aqueous diluted formulation only maintained stability for up to three days, then the CBD crystallized out of solution, and the precipitated CBD settled to the bottom of the formulation. This precipitation necessitates preparation of materials at the point of use and in small batch quantities over the course of multiple days, which presents logistical difficulties in the preparation and use of uniform materials for study or administration. Formulations prepared at point of use are totally inadequate for large-scale use, and would prevent a wider use of the lipophilic passengers in lipid particles. Given these challenges, investigations were directed to finding options for reducing or eliminating the crystallization observed in the formulation.

Initial endeavors to remediate the crystallization focused on improving solubility within the system and it was found that precisely controlled amounts of selected surfactants provided the desired improvements in both stability and solubility of the passenger, which in this case was CBD. These studies demonstrated that the precisely controlled surfactants yielded the desired improvement in reducing crystallization with no crystals observed in the samples after three-months storage at room temperature. This surfactant enhancing approach solved the challenges seen with the aqueous-diluted formulation and represented a novel composition with enhanced encapsulation of more difficult passenger molecules. Initiatives to develop a beverage type formulation using a phospholipid vesicle system specifically for cannabinoids also led to additional research into increasing the load of cannabinoids that can be incorporated into an aqueous delivery vehicle without degradation of the cannabinoid encapsulate.

Investigations then focused on the maximum amount of CBD that would be encapsulated into the aqueous system and at what point of aqueous dilution did the precipitation occur. As CBD is a lipophilic molecule with reasonable solubility in alcohol, adjunctive compounds were investigated to enhance the solubility and compatibility of CBD with the phospholipid technology as well as the aqueous phase of the system. It was found that the amount of the passenger molecule loaded into the phospholipid structures could be increased by including specific solubilizer compounds into the encapsulation phase, with the incorporation of certain surfactants being particularly efficacious, leading to improvements in encapsulation and remediation of the crystallization of cannabidiol observed in the original aqueous-based formulation used in early PK studies.

It was determined that use of these surfactants as stability-enhancing compounds not only prevented precipitation of the CBD passenger, but also allowed for greatly increased passenger molecule loading into the phospholipid vesicles with CBD concentrations increased more than a hundred-fold over the previous models. Using aqueous-based compositions could only accommodate up to 1-2 mg/mL of CBD as a passenger, whereas the enhanced system was shown to accommodate concentrations more than 100 times higher than the previous system. Cannabinoids concentrations up to 300 mg/mL are now achievable.

Surfactants are partly hydrophilic (water-soluble) and partly lipophilic (soluble in lipids, or oils) compounds that lower the surface tension (or interfacial tension) between two liquids, between a gas and a liquid, or between a liquid and a solid. Surfactants are usually organic compounds that are amphiphilic, consisting of a hydrophilic head group and a hydrophobic tail and they generally are suitable compounds for use in complex mixtures. The surfactants useful for the present invention exhibit a very low toxicity level and are acceptable for use in pharmaceuticals, cosmetics and food products.

Previous work had indicated that many surfactants would cause destabilization of lipid bilayers leading to collapse of the vesicles. Indeed surfactants, such as Triton X100 (nonoxynol-9), have been used specifically to disrupt nanolipid particles to release the encapsulated passenger molecules. It was believed that any added surfactant would interfere with the integrity of the lipid bilayer of the nanolipid particles and destabilize the system, thereby causing the nanolipid particles structures to collapse and release any encapsulated compound into the continuous phase of the preparation. The use of surfactants was, therefore, not expected to be compatible with phospholipid particles based on the original nanolipid particles development and approach. It has surprisingly now been found that specific alternative surfactants in precisely controlled amounts are able to advantageously influence the viability and stability of the lipid structures while also achieving increased encapsulation capacity and decreased precipitation of passenger molecules. When used in the method of the invention, these precisely controlled surfactants do not lead to collapse or destabilization of the vesicles.

Load-enhancing surfactants useful for the present invention include, but are not limited to, Polysorbates, PEG esters of hydrogenated castor oil, Polyethylene Glycols, Ethoxylated ether alcohols, Propylene Glycols, PPG esters, Sodium, Potassium or Ammonium Salts of Fatty Acids, and derivatives and combinations thereof. Optionally, the load enhancing compounds are PEG-40 hydrogenated castor oil and derivatives, Polysorbate (Tween) 20 and derivatives, Polysorbate (Tween) 80 and derivatives, and combinations thereof. In one embodiment of the invention, the load-enhancing compound is a PEG ester of hydrogenated castor oil. In one embodiment of the invention, the load-enhancing compound is PEG 40 hydrogenated castor oil. In one embodiment of the invention, the load-enhancing compound is Polysorbate (Tween) 20. In one embodiment of the invention, the load-enhancing compound is Polysorbate (Tween) 80. In one embodiment of the invention, the load-enhancing compound is a combination of PEG 40 hydrogenated castor oil and Polysorbate (Tween) 20 or Polysorbate (Tween) 80.

Composition

As disclosed herein, Surfactant-Enhanced Phospholipid Vesicles (SEPV) are phospholipid vesicles that employ a surfactant to complete the encapsulation process for lipophilic passenger substances which enhances the encapsulation efficiency and prevents precipitation of the passenger molecules. The Surfactant-Enhanced Phospholipid Vesicles comprise a phospholipid stock solution having phospholipids, ethanol and water, an ethanol diluent, a lipophilic passenger molecule and a load-enhancing surfactant component.

The phospholipid stock solution has a composition ratio of 75-89% ethanol, 10-20% phospholipids and 1-5% water, (w/w). Optionally, the phospholipid stock solution has a component ratio of 80% ethanol/17.75% phospholipids/2.25% water (w/w). Optionally, the ethanol used in the phospholipid stock is dehydrated 190 proof ethanol. Optionally, the phospholipids are derived from soy lecithin. Phospholipids are selected from phosphatidylcholine (PC), phosphatidylethanolamine (PE), phosphatidic acid (PA) and phosphatidylinositol (PI), and mixtures thereof. Optionally, phosphatidylcholine (PC) comprises at least 50% by weight of the phospholipid mixture. Optionally, phosphatidylcholine comprises 65% of the phospholipid total. Optionally, the ethanol diluent is dehydrated 190 proof ethanol. Optionally, up to 75% (w/w) ethanol diluent is added to the phospholipid stock solution prior to addition of or in combination with the passenger molecules.

The passenger molecules in the composition are preferably lipophilic substances. Passenger molecules that may benefit from enhanced encapsulation include, but are not limited to, cannabinoids, cannabidiol (CBD), tetrahydrocannabinol (THC), menthol, lidocaine, aspirin, ibuprofen, acetaminophen, antifungals, and retinoids. Optionally, the passenger molecule is one or more cannabinoid. In one embodiment of the invention, the passenger molecule is cannabidiol (CBD). In one embodiment of the invention, the passenger molecule is tetrahydrocannabinol (THC). In another embodiment of the invention, passenger molecules are a combination of cannabidiol (CBD) and tetrahydrocannabinol (THC).

Load-enhancing surfactants useful for the present invention include, but are not limited to, Polysorbates, PEG esters of hydrogenated castor oil, Polyethylene Glycols, Ethoxylated ether alcohols, Propylene Glycols, PPG esters, Sodium, Potassium or Ammonium Salts of Fatty Acids, and derivatives or combinations thereof. Optionally, the load-enhancing compound is one or more polysorbate and derivatives, PEG esters of hydrogenated castor oil and derivatives, or combination thereof. Optionally, the load enhancing compounds are PEG-40 hydrogenated castor oil and derivatives, Polysorbate (Tween) 20 and derivatives, Polysorbate (Tween) 80, and derivatives, or combinations thereof. In one embodiment of the invention, the load-enhancing compound is a PEG ester of hydrogenated castor oil. In one embodiment of the invention, the load-enhancing compound is PEG 40 hydrogenated castor oil. In one embodiment, the load-enhancing compound is Polysorbate (Tween) 20. In one embodiment, the load-enhancing compound is Polysorbate (Tween) 80. In one embodiment, the load-enhancing compound is a combination of PEG 40 hydrogenated castor oil and Polysorbate (Tween) 20 or Polysorbate (Tween) 80.

The Surfactant-Enhanced Phospholipid Vesicles (SEPV) composition optionally has 1%-50% (w/w) phospholipid stock solution, 10%-90% (w/w) ethanol, 1%-50% (w/w) passenger substance; and 1-50% (w/w) surfactant. Optionally, the composition has 10%-30% (w/w) phospholipid stock solution, 50%-75% (w/w) ethanol, 1%-20% (w/w) passenger substance; and 0.1%-25% (w/w) surfactant. Optionally, the composition has 14%-25.5% (w/w) phospholipid stock solution, 56%-69.6% (w/w) ethanol, 5%-10% (w/w) passenger substance; and 0.5%-20% (w/w) surfactant. In one embodiment of the invention, the composition has 14.00% (w/w) phospholipid stock solution, 56.00% (w/w) ethanol, 10.0% (w/w) passenger substance; and 20.00% (w/w) surfactant. In one embodiment of the invention, the composition has 25.5% (w/w) phospholipid stock solution, 69.0% (w/w) ethanol, 5.0% (w/w) passenger substance; and 0.5% (w/w) surfactant. In one embodiment of the invention, the composition has 24.0% (w/w) phospholipid stock solution, 69.60% (w/w) ethanol, 5.0% (w/w) passenger substance; and 1.4% (w/w) surfactant. Optionally, water can be used to dilute the finished encapsulate to achieve the desired passenger concentration. Optionally, water can be used to dilute the finished encapsulate at 1:1 up to 1:1000. Optionally, water can be used to dilute the finished composition at 1:10 up to 1:100.

Method of Making a Surfactant-Enhanced Phospholipid Vesicle Composition

A method of encapsulating passenger molecule compounds in Surfactant-Enhanced Phospholipid Vesicles (SEPV) is disclosed. The phospholipid stock for preparing the SEPV is manipulated by dilution with an ethanol solvent, combined with one or more desired passenger and then mixed with a load-enhancing surfactant to form a passenger encapsulate of SEPV. Optionally, the passenger encapsulate is for oral delivery. Optionally, the passenger encapsulate is for transdermal delivery. The passenger encapsulate may then be combined with additional ingredients to enhance flavor, appearance or usability of the preparation and may be diluted to achieve the desired dose for oral mucosa delivery or beverage delivery.

A method of encapsulating cannabinoid passenger molecules in Surfactant-Enhanced Phospholipid Vesicles (SEPV) is disclosed. The phospholipid stock for preparing the SEPV is manipulated by dilution with an ethanol solvent, combined with one or more desired cannabinoid passenger and then mixed with a load-enhancing surfactant to form a cannabinoid encapsulate of SEPV. Optionally, the cannabinoid encapsulate is for oral or transmucosal delivery. Optionally, the cannabinoid encapsulate of is for topical or transdermal delivery. The cannabinoid passenger encapsulate may then be combined with additional ingredients to enhance flavor, appearance or usability of the preparation. Optionally, the cannabinoid preparation is diluted to achieve the desired dose for oral or transmucosal or beverage delivery, or the desired dose for topical or transdermal delivery.

To make the Surfactant-Enhanced Phospholipid Vesicles (SEPV), a phospholipid stock solution is combined with an ethanol diluent and mixed until homogenous. The cannabinoid passenger substance is added to the ethanol-phospholipid mixture and blended until the cannabinoid passenger-stock mixture is homogenous with the cannabinoid passenger fully incorporated. A quantity of load-enhancing surfactant is then thoroughly combined with the cannabinoid passenger-stock mixture yielding a cannabinoid encapsulate of surfactant-enhanced phospholipid vesicles with cannabinoid passenger molecules encapsulated therein. The cannabinoid encapsulate may then be combined with additional ingredients to enhance flavor, appearance or usability of the preparation and may be diluted to achieve the desired dose for oral or transmucosal or beverage delivery, or the desired dose for topical or transdermal delivery.

The phospholipid stock used to make the Surfactant-Enhanced Phospholipid Vesicles (SEPV), is prepared by combining phospholipids with ethanol and stirring at ambient room temperature until dissolved. Optionally, the ethanol used in the phospholipid stock is dehydrated 190 proof ethanol. A small quantity of water having a pH of 5-8 is added to the ethanol/phospholipid mixture and stirred until an optically clear phospholipid stock solution results. The ratio of the components in the phospholipid stock solution ranges from 75-89% ethanol, 10-20% phospholipids and 1-5% (w/w) water. Optionally, the ratio of components in the phospholipid stock is 80% ethanol/17.75% phospholipids/2.25% water (w/w). Optionally, the phospholipids are derived from soy lecithin. Phospholipids are selected from phosphatidylcholine (PC), phosphatidylethanolamine (PE), phosphatidic acid (PA) and phosphatidylinositol (PI), and mixtures thereof. Optionally, phosphatidylcholine (PC) comprises at least 50% by weight of the phospholipid mixture. Optionally, phosphatidylcholine comprises 65% of the phospholipid total.

The phospholipid stock mixture is then combined with a quantity of ethanol, 1:1 to 1:100 (by volume) and stirred until the mixture is homogenous. Passenger molecules are added to the ethanol-diluted phospholipid stock mixture and mixed until the passenger is fully incorporated and the passenger-stock mixture is homogenous. The passenger-stock mixture is then combined with a quantity of surfactant, 1:1 to 1:100 (by volume) and mixed until a uniform composition having an opalescent appearance is achieved. The resulting composition has nano-sized surfactant-enhanced phospholipid vesicles sized from 25 nm to 200 nm in diameter. Optionally, the vesicles are sized from 80 nm to 130 nm. Optionally, the vesicles are about 80 nm in diameter.

Surfactants are used in the present invention as load-enhancing compounds that increase the concentration of one or more passenger molecule loaded into a phospholipid based nano-sized vesicle to concentrations greater than could be achieved without the enhancer and also maintains the structural integrity of the vesicles preventing precipitation of the encapsulated passenger. Load-enhancing surfactants useful for the present invention include, but are not limited to, Polysorbates, PEG esters of hydrogenated castor oil, Polyethylene Glycols, Ethoxylated ether alcohols, Propylene Glycols, PPG esters, Sodium, Potassium or Ammonium Salts of Fatty Acids, and derivatives or combinations thereof. Optionally, the load-enhancing compound is one or more of polysorbate and derivatives, PEG esters of hydrogenated castor oil and derivatives, or combinations thereof. Optionally, the load enhancing compounds are PEG-40 hydrogenated castor oil and derivatives, Polysorbate (Tween) 20 and derivatives, Polysorbate (Tween) 80 and derivatives, or combinations thereof. In one embodiment of the invention, the load-enhancing compound is a PEG ester of hydrogenated castor oil. In one embodiment of the invention, the load-enhancing compound is PEG 40 hydrogenated castor oil. In one embodiment, the load-enhancing compound is Polysorbate (Tween) 20. In one embodiment, the load-enhancing compound is Polysorbate (Tween) 80. In one embodiment, the load-enhancing compound is a combination of PEG 40 hydrogenated castor oil and Polysorbate (Tween) 20 or Polysorbate (Tween) 80.

Passengers Substances

Passenger that may be encapsulated in surfactant-enhanced phospholipid vesicles are preferably lipophilic substances. Passenger molecules that may benefit from enhanced encapsulation include, but are not limited to, cannabinoids, cannabidiol (CBD), tetrahydrocannabinol (THC), menthol, lidocaine, aspirin, ibuprofen, acetaminophen, antifungals, and retinoids. Optionally, the passenger is one or more cannabinoid. In one embodiment of the invention, the passenger molecule is cannabidiol (CBD). In one embodiment of the invention, the passenger molecule is tetrahydrocannabinol (THC). In another embodiment of the invention, passenger molecules are a combination of cannabidiol (CBD) and tetrahydrocannabinol (THC).

In one embodiment of the invention, the passenger molecule is a *Cannabis sativa*-derived compound. *Cannabis sativa*-derived substances can be derived from all varieties of *Cannabis sativa*, including hemp. In one embodiment of the invention, the passenger molecule is a *Cannabis indica*-derived compound. Organic solvents, such as ethanol, butane, and propane, can be used to extract *Cannabis*-derived substances, including cannabidiol (CBD), tetrahydrocannabinol (THC), flavonoids and terpenes. Cannabidiol (CBD) can also be extracted from hemp plant materials by a supercritical carbon dioxide extraction process, wherein phase changes induced in the $CO_2$, utilizing temperature and pressure, yield extracts free of toxic solvents. *Cannabis* varieties used for hemp production are one preferred source of CBD because of a high concentration of CBD with a low concentration of THC in materials from those plants.

*Cannabis sativa* has over 483 known compounds, over 60 of which are classified as cannabinoids, many of which have mental and physical effects, which may be used in the present invention, including tetrahydrocannabinol (THC) and cannabidiol (CBD). Cannabidiol (CBD) is one of the most prevalent chemical compounds in the cannabis plant and typically does not produce psychotropic effects. *Cannabis sativa*-derived compounds also include numerous non-cannabinoid compounds. Optionally, the composition of surfactant-enhanced phospholipid vesicles has one or more cannabinoid passenger. Optionally, the composition of surfactant-enhanced phospholipid vesicles has one or more non-cannabinoid passenger. Optionally, the composition of surfactant-enhanced phospholipid vesicles has one or more cannabinoid passenger and one or more non-cannabinoid passenger.

In one embodiment of the invention, the passenger molecule is a non-cannabinoid *Cannabis*-derived compound. Among the non-cannabinoid *Cannabis*-derived compounds are a variety of terpenes and flavonoids. Terpenes are oils secreted from the plant which give the plant its characteristic odor and produce physical effects similar to those seen with CBD. Flavonoids are phytonutrients that are pharmacologically active having individual medicinal benefits and enhancing the effects of other *Cannabis*-derived compounds. Flavonoids and terpenes may be added to the preparations in addition to the cannabinoids to improve the uptake, or enhance or regulate the effects of one or more of the cannabinoid active ingredients. Optionally, the composition of surfactant-enhanced phospholipid vesicles has one terpene or flavonoid non-cannabinoid compound encapsulated therein.

Cannabinoids other than CBD and THC can be derived from *Cannabis sativa* and *Cannabis indica* and may also be used as passenger molecules in the disclosed invention. Most of the other cannabinoids are non-psychoactive or mildly psychoactive, and have physiological effects similar to the effects seen for CBD. These other cannabinoids may work synergistically to enhance the effects of CBD and THC. Other cannabinoids that may be used as passenger molecules in the disclosed invention include, but are not limited to: Cannabigerol (CBG), Cannabidiolic Acid (CBDA), Tetrahydrocannabinolic Acid (THCA), Cannabinol (CBN), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol monomethyl ether (CBGM), Cannabielsoin (CBE), Cannabicitran (CBT), and combinations thereof. Synthetically-derived cannabinoids may also be used as passenger molecules.

Whole plant extracts of *Cannabis* spp. may also be used as passenger molecules in the disclosed invention, and may be beneficial because non-cannabinoid plant compounds, such as the terpenes and flavonoids, are present in a whole plant sample. Whole plant cannabis extracts can also be encapsulated in the surfactant-enhanced phospholipid vesicles. Whole plant cannabis extract is an oily or waxy material that is soluble in lipids and alcohols. Whole plant extracts will vary in the amount of cannabinoids in the extract depending on whether the extract is prepared from marijuana-grade cannabis or industrial-grade hemp. Both types of whole plant extracts will have cannabinoids, terpenes and flavonoids, with the primary difference being the concentrations of CBD and THC in the final extract.

CBD and THC extracts can be advantageously used in combination as passengers in the surfactant-enhanced phospholipid vesicle composition. CBD and THC are extracted from cannabis plants as separate isolates, either as oils or crystals, or optionally, are synthetically-derived, and then combinations of these extracts can be encapsulated in the surfactant-enhanced phospholipid vesicles. The CBD and THC can be combined and encapsulated in the surfactant-enhanced phospholipid vesicle composition in the same step, or the CBD and THC can be individually encapsulated in surfactant-enhanced phospholipid vesicles and then combined into a single composition.

Oral delivery means that may be used in the disclosed invention include, but are not limited to: liquids, as drops, sprays, aerosols, or shots, gels, pastes, lozenges, gums, gummy candies, hard candies, orally dissolving strips, tablets, and swish and swallow preparations. The preparation may be applied under the tongue (sublingual), inside the cheeks (buccal), or inside the oral cavity. Oral delivery means may also include preparations that may be consumed as a beverage type delivery means, such as a drinkable beverage, shot, or swish and swallow type preparation.

Preparations for oral delivery may also incorporate additional non-cannabis compounds, such as sweeteners including nutritive and non-nutritive sweeteners, flavoring agents, vitamins, minerals, herbal ingredients, distillates, and/or extracts, fruit and vegetable ingredients and/or extracts, amino acids, nutraceutical ingredients; and combinations thereof, which may improve functionality of the cannabinoid encapsulate or provide additional benefits to the user. Examples of ingredients that may be used advantageously for an oral preparation include, but are not limited to: stevia extract, sugar, yerba mate, green coffee bean extract, monk fruit extract, citric acid, potassium sorbate, black pepper extract, lemon extract, ginger, tulsi distillate, turmeric, theanine, xanthan gum, and glycerin. Preparations for oral delivery may also include excipient ingredients to improve appearance, application, taste, smell, longevity, stabilization, or adherence of the preparation.

Preparations for oral delivery are made by combining a phospholipid stock having ethanol, phospholipids and water, with an ethanol diluent, and mixed until homogenous. Phospholipids include phospholipids derived from lecithin. One or more *Cannabis*-derived passenger is added to the combined ethanol-stock mixture and blended until the passenger-stock mixture is homogenous and the *Cannabis*-derived passenger is fully solubilized. The load-enhancing surfactant compound is added to the passenger-stock mixture and blended until a homogenous mixture of surfactant-enhanced phospholipid vesicles having encapsulated cannabis derived passenger encapsulated therein is achieved.

Cannabinoids encapsulated in surfactant-enhanced phospholipid vesicles (SEPV) for oral delivery is disclosed. The surfactant-enhanced phospholipid vesicles are formulated for delivery of the cannabinoid compounds to the oral cavity or mucosa of a subject. Optionally, the oral preparation is for application of the SEPV composition to the oral, sublingual or buccal mucosa of a subject. Optionally, the SEPV composition is applied to the oral cavity as liquid drops, sprays, aerosols, or shots, gels, pastes, lozenges, gums, gummy candies, hard candies, orally dissolving strips, tablets, and swish and swallow preparations. These types of preparations are held in the mouth, under the tongue, or allowed to disintegrate for up to several minutes prior to swallowing. Optionally, the oral delivery is as a liquid preparation in a drinkable format, such as a beverage, shot, or swish and swallow preparation. Optionally, the liquid preparation is a drinkable format, such as a beverage (typically more than 1.5 ounce), or as a shot (typically 1.5 ounce or less), or swish and swallow preparation (typically 1.0 ounce or less).

Cannabinoids encapsulated in surfactant-enhanced phospholipid vesicles for topical or transdermal delivery is disclosed. The surfactant-enhanced phospholipid vesicles are formulated for delivery of the *Cannabis*-derived compounds to an epidermal area of a subject. Optionally, the delivery route is topical or transdermal via a topically applied preparation, such as a topically applied cream, lotion, ointment, wax, topically applied spray, gel, balm, transdermal patch, or other transdermal application means to an epidermal area.

Method of Using

Methods of using surfactant-enhanced phospholipid vesicles with encapsulated passenger molecules is disclosed. Methods for delivery comprise providing a passenger encapsulate having one or more passenger molecules encapsulated in surfactant-enhanced phospholipid vesicles capable of delivering the passenger compound to a subject, preparing the passenger encapsulate for delivery by mixing the passenger encapsulate with diluents or other constituents to reach the desired dosage of passenger compound, and administering the passenger encapsulate preparation to a subject. Optionally, the route of delivery is oral, via a transmucosal preparation, a sublingual preparation, a buccal preparation, or an oral beverage preparation. Optionally, the delivery route is topical or transdermal via a topically applied preparation means to an epidermal area. Passenger molecules in the passenger encapsulate are preferably lipophilic substances. Passenger molecules that may benefit from enhanced encapsulation include, but are not limited to, cannabinoids, cannabidiol (CBD), tetrahydrocannabinol (THC), menthol, lidocaine, aspirin, ibuprofen, acetaminophen, antifungals, and retinoids.

Optionally, the passenger encapsulate is applied to the oral cavity as liquid drops, sprays, aerosols, or shots, gels, pastes, lozenges, gums, gummy candies, hard candies, orally dissolving strips, tablets, and swish and swallow preparations. These types of preparations are held in the mouth, under the tongue or allowed to disintegrate for up to several minutes prior to swallowing. Optionally, the oral delivery is as a liquid preparation in a drinkable format, such as a beverage, shot, or swish and swallow preparation. Optionally, the liquid preparation is a drinkable format, such as a beverage (typically more than 1.5 ounce) or as a shot (typically 1.5 ounce or less), or swish and swallow preparation (typically 1.0 ounce or less).

Optionally, the delivery route for the passenger encapsulate is transdermal via a topically applied preparation, such as a topically applied cream, lotion, ointment, wax, topically applied spray, gel, balm, transdermal patch or other transdermal application means to an epidermal area.

Methods of using surfactant-enhanced phospholipid vesicles with encapsulated cannabinoid passenger molecules is disclosed. Methods for delivery comprise providing a cannabinoid encapsulate having one or more cannabinoid passenger molecules encapsulated in surfactant-enhanced phospholipid vesicles capable of delivering the cannabinoid to a subject, preparing the cannabinoid encapsulate for delivery by mixing the cannabinoid encapsulate with diluents, excipients, or other constituents to reach the desired dosage of cannabinoid compound, and administering the cannabinoid encapsulate preparation to a subject.

Optionally, the passenger is one or more cannabinoid. Optionally, the passenger is one or more *Cannabis*-derived substance. Optionally, the cannabinoids are synthetically-derived. In one embodiment of the invention, the passenger molecule is cannabidiol (CBD). In one embodiment of the invention, the passenger molecule is tetrahydrocannabinol (THC). In another embodiment of the invention, passenger molecules are a combination of cannabidiol (CBD) and tetrahydrocannabinol (THC).

Optionally, the route of delivery for the cannabinoid encapsulate is oral, via a transmucosal preparation, a sublingual preparation, a buccal preparation, or an oral beverage preparation. These types of preparations may be held in the mouth, under the tongue or allowed to disintegrate for up to several minutes prior to swallowing. Optionally, the oral delivery is as a liquid preparation in a drinkable format, such as a beverage, shot, or swish and swallow preparation. Optionally, the liquid preparation is a drinkable format, such as a beverage (typically more than 1.5 ounce) or as a shot (typically 1.5 ounce or less), or swish and swallow preparation (typically 1.0 ounce or less).

Optionally, the delivery route for the cannabinoid encapsulate is topical or transdermal via a topically applied preparation, such as a topically applied cream, lotion, ointment, wax, topically applied spray, gel, balm, transdermal patch, or other transdermal application means to an epidermal area.

Cannabinoid substances can be administered in dosages ranging up to 1200 mg per day. Cannabinoid encapsulates have a *Cannabis sativa*-derived substance concentration of 3 mg/mL to 300 mg/mL. *Cannabis sativa*-derived substances which are encapsulated in surfactant-enhanced phospholipid vesicles are administered in dosages ranging up from 1 mg to 300 mg per day in single or divided doses or any dose between 1 mg and 300 mg per day. Optionally, dosages range from 1 mg to 100 mg per day in single or divided doses. Optionally, dosages range from 10 mg to 100 mg per day in single or divided doses. Optionally, the dosages range from 1 mg to 20 mg per day in a single or divided dose.

Cannabinoid encapsulated in surfactant-enhanced phospholipid vesicles for oral delivery is disclosed. The surfactant-enhanced phospholipid vesicles are formulated for delivery of the *Cannabis*-derived compounds to the oral cavity or oral mucosa of a subject. Optionally, the oral delivery is application of the cannabinoid encapsulate to the oral, sublingual or buccal mucosa of a subject. Optionally, the cannabinoid encapsulate is applied to the oral cavity as liquid drops, sprays, aerosols, or shots, gels, pastes, lozenges, gums, gummy candies, hard candies, orally dissolving strips, tablets, and swish and swallow preparations. These types of preparations are held in the mouth, under the tongue or allowed to disintegrate for up to several minutes prior to swallowing. Optionally, the oral delivery is as a liquid preparation in a drinkable format, such as a beverage, shot, or swish and swallow preparation. Optionally, the liquid preparation is a drinkable format, such as a beverage (typically more than 1.5 ounce) or as a shot (typically 1.5 ounce or less), or swish and swallow preparation (typically 1.0 ounce or less).

In one embodiment, a phospholipid stock having phospholipids, ethanol and water is combined with an ethanol diluent and blended until homogenous. Crystalline CBD having greater than 99% purity is combined with the ethanol-phospholipid stock until the CBD passenger-stock mixture is homogenous and the CBD is uniformly distributed therein. A quantity of load-enhancing surfactant is combined with the CBD passenger-stock mixture and blended until a homogenous cannabinoid encapsulate of surfactant-enhanced phospholipid vesicles with CBD encapsulated therein is achieved. Phospholipids used in the phospholipid stock are optionally derived from lecithin. Phospholipids used in the phospholipid stock are optionally derived from soy lecithin. The CBD cannabinoid encapsulate may then be combined or diluted with an aqueous or non-aqueous delivery system without disruption of the surfactant-enhanced phospholipid vesicles.

EXAMPLES

An exemplary composition is detailed in Table 1, below. Examples shown herein are not meant to limit the combinations or concentrations of components for the composition for the present invention, but are merely representative ways in which the components may be used. The example composition has been shown to provide greater physical stability than predecessor compositions as evidenced by no crystallization after more than three months ambient room temperature storage. The loading enhancement herein can be applied to all forms of delivery vehicles, inclusive of, but not limited to, topical, oral, mucosal, vaginal, rectal, beverage, parenteral, and inhalation. Load enhancing compounds include but are not limited to Polysorbates, PEG esters of hydrogenated castor oil, Polyethylene Glycols, Ethoxylated ether alcohols, Propylene Glycols, PPG esters, Sodium, Potassium or Ammonium Salts of Fatty Acids, and derivatives thereof, etc. In one embodiment of the invention, the load-enhancing compound is a PEG ester of hydrogenated castor oil. In one embodiment of the invention, the load-enhancing compound is PEG-40 hydrogenated castor oil. In one embodiment of the invention, the load-enhancing compound is Polysorbate (Tween) 20. In one embodiment of the invention, the load-enhancing compound is Polysorbate (Tween) 80. In one embodiment of the invention, the load-enhancing compound is a combination of PEG-40 hydrogenated castor oil and Polysorbate (Tween) 20 or Polysorbate (Tween) 80.

TABLE 1

Passenger Molecule Loading Enhancing Composition

| Ingredient | Percentage (v/v) | NLP Range | Purpose |
|---|---|---|---|
| PL Stock (Lecithin, Ethanol, Water) | ~1-50% | ~1-20 | Encapsulation |
| Ethanol | ~10-90% | ~1-90 | Diluent |
| Passenger Molecule[1] | ~1-50% | Not claimed | Delivered molecule |
| Loading Enhancer[2] | ~1-80% | Not claimed | Passenger loading Enhancement |
| Water | ~1-99.9% | | Diluent for finished composition |

[1] Passenger molecule examples include but are not limited to cannabinoids, cannabidiol, tetrahydrocannabinol, menthol, lidocaine, aspirin, ibuprofen, acetaminophen, antifungals, retinoids.
[2] Load enhancing compounds include but are not limited to Polysorbates, PEG esters of hydrogenated castor oil, Polyethylene Glycols, Sodium/Potassium/Ammonium Salts of Fatty Acids and derivatives, etc.

The examples below are illustrative examples that are envisioned for the disclosed invention and are not intended to be the only examples, embodiments, formulations, compositions, or concentrations that may be used with the disclosed invention.

Example 1: Illustrative Solubilized CBD in the Cannabinoid Encapsulate

Product Name: 100 mg/g CBD Concentrate
Batch Size 150.00

| Phase/DZ # | Ingredient | INCI Name | % | Wt. |
|---|---|---|---|---|
| A DZ 4130 | Phospholipid Stock | Alcohol, Lecithin, Water | 14.00 | 21.00 |
| A DZ 2330 | Ethanol | Alcohol | 56.00 | 84.00 |
| A DZ 4730 | Cannabidiol | Cannabidiol | 10.00 | 15.00 |
| A DZ 4800 | PEG-40 Hydrogenated Castor Oil | PEG-40 Hydrogenated Castor Oil | 20.00 | 30.00 |
| | | | 100.00 | 150.00 |

Steps Procedure:

1. In a suitable vessel, add the phospholipid stock and ethanol. Mix together for 5-10 mins.
2. Add CBD to mixing solution. Allow to mix for 15-20 mins or until all CBD has fully dissolved.
3. Once solution is homogenous. Add PEG-40 Hydrogenated Castor Oil. Allow to mix for 15-20 minutes or until homogenous.
4. Dilute an aliquot of final product 1:1000 and test for PSA.

The table below is an illustrative example of component concentration shown in descending order for a sample of passenger encapsulate prepared according to the present invention. The top section of the chart shows the solvent broken down by the percentage of ethanol solvent in the phospholipid stock solution and the percentage of ethanol solvent used as a diluent prior to incorporating the passenger into the phospholipid stock. The bottom section of the table shows the combined concentrations in descending order for a representative sample of a CBD passenger encapsulate.

Example 2: Illustrative Product Composition in the Cannabinoid Encapsulate

| Component | INCI Name | % in Product | % Breakdown |
|---|---|---|---|
| Solvent (diluent) | Alcohol | 56.00 | 56.00 |
| Surfactant | PEG-40 Hydrogenated Castor Oil | 20.00 | 20.00 |
| Solvent (stock) | Alcohol | 14.00 | 11.26 |
| Passenger | Cannabidiol | 10.00 | 10.00 |
| Phospholipid (stock) | Lecithin | | 2.42 |
| Water (stock) | Water | | 0.32 |

| Final Breakdown | Final % Breakdown |
|---|---|
| Alcohol | 67.26 |
| PEG-40 Hydrogenated Castor Oil | 20.00 |
| Cannabidiol | 10.00 |
| Lecithin | 2.42 |
| Water | 0.32 |
| | 100.00 |

The chart below illustrates several possible examples of oral preparations that may be prepared using a passenger encapsulate prepared according to the present invention. The passenger encapsulate used in these examples is a THC encapsulate having about 5% THC that is diluted to around 0.5% prior to use in the final preparation.

Example 3: Illustrative Oral Preparations Using the Cannabinoid Encapsulate

| Composition | Batch 1 | Batch 2 | Batch 3 Chill #2 | Energy #2 |
|---|---|---|---|---|
| Water | 98.162 | 96.81 | 70.00 | QS |
| Sugar |  |  | 7.00 | 7.00 |
| Stevia Extract |  | 0.25 |  |  |
| Yerba Mate |  |  |  | 0.55 |
| Green Coffee Bean |  |  |  | 0.085 |
| Monk Fruit Extract 50% |  |  | 0.01 | 0.01 |
| Citric Acid | 0.67 | 0.67 | 0.45 | 0.18 |
| Potassium Sorbate | 0.10 | 0.10 | 0.10 | 0.10 |
| Black pepper Extract |  |  | 0.02 |  |
| Lemon Extract |  |  |  | 0.10 |
| Ginger |  |  | 0.07 | 0.07 |
| Tulsi Distillate |  |  | 0.10 |  |
| Turmeric Powder |  |  | 0.25 |  |
| Theanine |  |  | 0.10 |  |
| Water |  |  | 2.50 |  |
| EtOH | 0.3574 |  | 0.02 |  |
| EtOH Stock | 0.26 |  | 0.10 |  |
| Xanthan Gum | 0.05 | 0.15 | 0.20 | 0.10 |
| Glycerin | 0.50 | 1.50 | 1.50 | 1.50 |
| THC Encapsulate (adjusted for potency of THC) | 0.5179 | 0.516 | 0.442 | 0.442 |
| THC Encapsulate |  |  |  |  |
| THC | 5.00 | 5.00 | 5.00 | 5.00 |
| EtOH | 69.00 | 69.60 | 69.60 | 69.60 |
| EtOH Stock | 25.50 | 24.00 | 24.00 | 24.00 |
| PEG-40 Hydrogenated Castor Oil | 0.50 | 1.00 | 1.00 | 1.00 |
| Polysorbate 20 |  | 0.40 | 0.40 | 0.40 |
| QS Water |  |  |  |  |

The illustrative oral preparations in Example 3 are examples where the composition of Surfactant-Enhanced Phospholipid Vesicles with a THC passenger incorporated within the vesicles is combined with additional ingredients suitable for oral delivery of the passenger substance in a format, such as a beverage (volume variable) or a shot (about 1 ounce). In the example preparation, a composition of THC encapsulate having about 5.00% THC is prepared according the present invention then combined with additional ingredients, and diluted with water to a desired final volume having the desired final THC concentration.

Preparations for oral delivery as a beverage or shot may include a variety of desired ingredients, such as sweeteners, flavoring agents, vitamins, minerals, herbal ingredients, fruit or vegetable extracts, herb or spice extracts, caffeine, amino acids, and nutraceutical ingredients, as well as excipient ingredients to improve appearance, application, adherence, dilution, stability, or longevity of the preparation. Examples of ingredients that may be used advantageously for an oral preparation include, but are not limited to: stevia extract, sugar, yerba mate, green coffee bean extract, monk fruit extract, citric acid, potassium sorbate, black pepper extract, lemon extract, ginger, tulsi distillate, turmeric, theanine, xanthan gum, and glycerin.

The examples showing compositions with enhanced loading, product compositions and oral preparations presented herein are representative examples only. The method of the invention is applicable to other types of passenger substances and these examples are not meant to constitute the entire range of passenger substances or load-enhancing compositions, product compositions or oral preparations that may be used in the method disclosed herein.

The invention claimed is:

1. A composition comprising: a cannabinoid encapsulate having one or more cannabinoid substance selected from cannabidiol (CBD), tetrahydrocannabinol (THC), a whole plant extract of *Cannabis sativa*, a whole plant extract of *Cannabis indica*, and combinations thereof, encapsulated in a surfactant-enhanced phospholipid vesicle (SEPV) sized from 25 nm to 200 nm having phospholipids, ethanol, water, and one or more surfactant, wherein said one or more surfactant comprises up to 25% (w/w) of said cannabinoid encapsulate, said water comprises less than 2% (w/w) of said cannabinoid encapsulate, and said cannabinoid encapsulate has a cannabinoid concentration of 3 mg/mL to 300 mg/mL.

2. The composition of claim 1, wherein the surfactant is selected from Polysorbates, Polysorbate 20, Polysorbate 80, PEG esters of hydrogenated castor oil, PEG-40 hydrogenated castor oil, Polyethylene Glycols and derivatives thereof, Propylene Glycols and derivatives thereof, Sodium, Potassium or Ammonium Salts of Fatty Acids, and derivatives or combinations thereof.

3. The composition of claim 2, wherein the surfactant is Polysorbate 80, PEG-40 hydrogenated castor oil, or combinations thereof.

4. The composition of claim 2, wherein the surfactant is PEG-40 hydrogenated castor oil.

5. The composition of claim 2, wherein the surfactant is Polysorbate 80.

6. The composition of claim 1, wherein the surfactant comprises 0.5% to 20% (w/w) of the cannabinoid encapsulate.

7. The composition of claim 1, wherein the surfactant-enhanced phospholipid vesicles have less than 2% (w/w) water.

8. The composition of claim 1, wherein the cannabinoid substance is cannabidiol (CBD).

9. The composition of claim 1, wherein the cannabinoid substance is tetrahydrocannabinol (THC).

10. The composition of claim 1, wherein the cannabinoid substance is a combination of cannabidiol (CBD) and tetrahydrocannabinol (THC).

11. The composition of claim 1, wherein the composition is formulated for oral delivery, transmucosal administration, topical, or transdermal administration.

12. The composition of claim 1, wherein said one or more cannabinoid substance is a *Cannabis sativa*-derived cannabinoid, *Cannabis indica*-derived cannabinoid, a synthetically derived cannabinoid, or combinations thereof.

13. A composition comprising one or more cannabinoid substance selected from cannabidiol (CBD), tetrahydrocannabinol (THC), *Cannabis*-derived terpenes, *Cannabis*-derived flavonoids, a whole plant extract of *Cannabis sativa*, a whole plant extract of *Cannabis indica* and combinations thereof, encapsulated in surfactant-enhanced phospholipid vesicles sized from 25 nm to 200 nm, said surfactant-enhanced phospholipid vesicles comprising phospholipids, ethanol, less than 2% water (w/w), and up to 25% (w/w) of one or more surfactant selected from polysorbates and derivatives, PEG esters of hydrogenated castor oil and derivatives, and combinations thereof.

14. The composition of claim 13, wherein the concentration of cannabinoid substance encapsulated in the surfactant-enhanced phospholipid vesicles is from 3 mg/mL to 300 mg/mL.

15. The composition of claim 13, wherein the surfactant is Polysorbate 20, Polysorbate 80, PEG-40 hydrogenated castor oil, or combinations thereof.

16. The composition of claim 13 wherein said one or more surfactant comprises 0.5% to 20% (w/w) of said surfactant-enhanced phospholipid vesicles.

17. The composition of claim 13, wherein the surfactant-enhanced phospholipid vesicles have less than 2% (w/w) water.

18. The composition of claim 13, wherein the cannabinoid substance is cannabidiol (CBD).

19. The composition of claim 13, wherein the cannabinoid substance is tetrahydrocannabinol (THC).

20. The composition of claim 13, wherein the cannabinoid substance is a combination of cannabidiol (CBD) and tetrahydrocannabinol (THC).

21. The composition of claim 13, wherein said one or more cannabinoid substance is a *Cannabis sativa*-derived cannabinoid, *Cannabis indica*-derived cannabinoid, a synthetically derived cannabinoid, or combinations thereof.

22. The composition of claim 13, wherein said surfactant-enhanced phospholipid vesicles with the encapsulated cannabinoid substance are formulated for administration to the oral cavity of a subject for oral delivery or transmucosal uptake of the cannabinoid substance.

23. A composition comprising one or more lipophilic passenger substance encapsulated in surfactant-enhanced phospholipid vesicles sized from 25 nm to 200 nm, said lipophilic passenger substance concentration being from 3.0 mg/mL to 300 mg/mL, said surfactant-enhanced phospholipid vesicles having one or more surfactant, phospholipids, ethanol, and water, wherein said one or more surfactant is up to 25% (w/w) of the composition, and said water is less than 2% (w/w) of the composition.

24. The composition of claim 23, wherein the lipophilic passenger substance is selected from Cannabidiol (CBD), Tetrahydrocannabinol (THC), Cannabigerol (CBG), Cannabidiolic Acid (CBDA), Tetrahydrocannabinolic Acid (THCA), Cannabinol (CBN), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol monomethyl ether (CBGM), Cannabielsoin (CBE), Cannabicitran (CBT), *Cannabis*-derived terpenes, *Cannabis*-derived flavonoids, a whole plant extract of *Cannabis sativa*, a whole plant extract of *Cannabis indica*, menthol, lidocaine, aspirin, ibuprofen, acetaminophen, antifungals, retinoids and combinations thereof.

25. The composition of claim 23, wherein the surfactant is Polysorbate 80, PEG-40 hydrogenated castor oil, or combinations thereof.

26. The composition of claim 23, wherein the lipophilic passenger substance is Cannabidiol (CBD), Tetrahydrocannabinol (THC), or a combination thereof.

* * * * *